United States Patent
Goldbrunner et al.

(10) Patent No.: US 9,532,982 B2
(45) Date of Patent: Jan. 3, 2017

(54) PHARMACEUTICAL COMBINATION COMPRISING A PHOSPHATIDYLINOSITOL 3-KINASE INHIBITOR AND/AN AROMATASE INHIBITOR

(71) Applicants: Michael Goldbrunner, Binzen (DE); Xizhong Huang, Southborough, MA (US)

(72) Inventors: Michael Goldbrunner, Binzen (DE); Xizhong Huang, Southborough, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/429,367

(22) PCT Filed: Sep. 18, 2013

(86) PCT No.: PCT/US2013/060292
§ 371 (c)(1),
(2) Date: Mar. 19, 2015

(87) PCT Pub. No.: WO2014/047109
PCT Pub. Date: Mar. 27, 2014

(65) Prior Publication Data
US 2015/0231124 A1 Aug. 20, 2015

Related U.S. Application Data

(60) Provisional application No. 61/703,533, filed on Sep. 20, 2012, provisional application No. 61/708,070, filed on Oct. 1, 2012.

(51) Int. Cl.
A61K 31/4439 (2006.01)
A61K 31/5685 (2006.01)
A61K 31/4196 (2006.01)

(52) U.S. Cl.
CPC ........ *A61K 31/4439* (2013.01); *A61K 31/4196* (2013.01); *A61K 31/5685* (2013.01)

(58) Field of Classification Search
None
See application file for complete search history.

(56) References Cited

U.S. PATENT DOCUMENTS

2010/0105711 A1  4/2010  Fairhurst et al.

FOREIGN PATENT DOCUMENTS

WO    WO 2010/029082 A1    3/2010

OTHER PUBLICATIONS

Glück, et al., Am. J. Health-Syst. Pharm., 68:1699 (Sep. 15, 2011).*

* cited by examiner

*Primary Examiner* — Michael Barker
(74) *Attorney, Agent, or Firm* — Michelle A. Han

(57) ABSTRACT

The present invention relates to a pharmaceutical combination comprising a 2-carboxamide cycloamino urea derivative compound of formula (I) and at least one aromatase inhibitor for the treatment of cancer; the uses of such combinations in the treatment of cancer; and to a method of treating warm-blooded animals including humans suffering cancer by administering to said animal in need of such treatment an effective dose of a 2-carboxamide cycloamino urea derivative compound of formula (I) in combination with at least one aromatase inhibitor.

4 Claims, 2 Drawing Sheets

Figure 1

Synergy Score: 2.1

Figure 2

Synergy Score: 4.6

PHARMACEUTICAL COMBINATION COMPRISING A PHOSPHATIDYLINOSITOL 3-KINASE INHIBITOR AND/AN AROMATASE INHIBITOR

FIELD OF THE INVENTION

The present invention relates to a pharmaceutical combination comprising a 2-carboxamide cycloamino urea derivative compound of formula (I) and at least one aromatase inhibitor for the treatment of cancer; the uses of such combinations in the treatment of cancer; and to a method of treating warm-blooded animals including humans suffering from cancer by administering to said animal in need of such treatment an effective dose of a 2-carboxamide cycloamino urea derivative compound of formula (I) in combination with at least one aromatase inhibitor.

BACKGROUND OF THE INVENTION

The PI3K/Akt/mTOR pathway is an important, tightly regulated survival pathway for the normal cell. Phosphatidylinositol 3-kinases (PI3Ks) are widely expressed lipid kinases that catalyze the transfer of phosphate to the D-3' position of inositol lipids to produce phosphoinositol-3-phosphate (PIP), phosphoinositol-3,4-diphosphate (PIP$_2$) and phosphoinositol-3,4,5-triphosphate (PIP$_3$). These products of the PI3K-catalyzed reactions act as second messengers and have central roles in key cellular processes, including cell growth, differentiation, mobility, proliferation and survival.

Of the two Class 1 PI3Ks, Class 1A PI3Ks are heterodimers composed of a catalytic p110 subunit ($\alpha$, $\beta$, $\delta$ isoforms) constitutively associated with a regulatory subunit that can be p85$\alpha$, p55$\alpha$, p50$\alpha$, p85$\beta$ or p55$\gamma$. The Class 1B sub-class has one family member, a heterodimer composed of a catalytic p110$\gamma$ subunit associated with one of two regulatory subunits, p101 or p84 (Fruman et al., *Annu Rev. Biochem.* 67:481 (1998); Suire et al., *Curr. Biol.* 15:566 (2005)).

In many cases, PIP2 and PIP3 recruit AKT to the plasma membrane where it acts as a nodal point for many intracellular signaling pathways important for growth and survival (Fant) et al., *Cell* 69:413-423(1992); Bader et al., *Nature Rev. Cancer* 5:921 (2005); Vivanco and Sawyer, *Nature Rev. Cancer* 2:489 (2002)). Aberrant regulation of PI3K, which often increases survival through AKT activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110$\alpha$ isoform, PIK3CA, and for AKT are amplified and increased protein expression of their gene products has been demonstrated in several human cancers. Further, somatic missense mutations in PIK3CA that activate downstream signaling pathways have been described at significant frequencies in a wide diversity of human cancers (Kang at el., *Proc. Natl. Acad. Sci. USA* 102:802 (2005); Samuels et al., *Science* 304:554 (2004); Samuels et al., *Cancer Cell* 7:561-573 (2005)). Thus, inhibitors of PI3K alpha are known to be of particular value in the treatment of cancer and other disorders.

In spite of numerous treatment options for cancer patients, there remains a need for effective and safe therapeutic agents and a need for their preferential use in combination therapy. The specific 2-carboxamide cycloamino urea derivative compounds of formula (I) are novel compounds that selectively inhibit the p110-$\alpha$ isoform of PI3K. It has been surprisingly discovered that these specific compounds of formula (I) have new beneficial effects, e.g. synergistic interaction, when used in combination with aromatase inhibitors for treatment of cancer. It is believed that this combination therapy will be beneficial in provoking strong anti-proliferative activity and/or strong antitumor response for the treatment of cancer.

SUMMARY OF THE INVENTION

The present invention relates to a pharmaceutical combination comprising (a) a compound of formula (I), (I)

wherein
A represents a heteroaryl selected from the group consisting of:

R$^1$ represents one of the following substituents: (1) unsubstituted or substituted, preferably substituted C$_1$-C$_7$-alkyl, wherein said substituents are independently selected from one or more, preferably one to nine of the following moieties: deuterium, fluoro, or one to two of the following moieties C$_3$-C$_5$-cycloalkyl; (2) optionally substituted C$_3$-C$_5$-cycloalkyl wherein said substituents are independently selected from one or more, preferably one to four of the following moieties: deuterium, C$_1$-C$_4$-alkyl (preferably methyl), fluoro, cyano, aminocarbonyl; (3) optionally substituted phenyl wherein said substituents are independently selected from one or more, preferably one to two of the following moieties: deuterium, halo, cyano, C$_1$-C$_7$-alkyl, C$_1$-C$_7$alkylamino, di(C$_1$-C$_7$-alkyl)amino, C$_1$-C$_7$-alkylaminocarbonyl, di(C$_1$-C$_7$alkyl)aminocarbonyl, C$_1$-C$_7$-alkoxy; (4) optionally mono- or di-substituted amine; wherein said substituents are independently selected from the following moieties: deuterium, C$_1$-C$_7$-alkyl (which is unsubstituted or substituted by one or more substituents selected from the group of deuterium, fluoro, chloro, hydroxy), phenylsulfonyl (which is unsubstituted or substituted by one or more, preferably one, C$_1$-C$_7$-alkyl, C$_1$-C$_7$-alkoxy, di(C$_1$-C$_7$-alkyl) amino-C$_1$-C$_7$-alkoxy); (5) substituted sulfonyl; wherein said substituent is selected from the following moieties: C$_1$-C$_7$-alkyl (which is unsubstituted or substituted by one or more substituents selected from the group of deuterium, fluoro), pyrrolidino, (which is unsubstituted or substituted by one or more substituents selected from the group of deuterium, hydroxy, oxo; particularly one oxo); (6) fluoro, chloro;

$R^2$ represents hydrogen;

$R^3$ represents (1) hydrogen, (2) fluoro, chloro, (3) optionally substituted methyl, wherein said substituents are independently selected from one or more, preferably one to three of the following moieties: deuterium, fluoro, chloro, dimethylamino, or a pharmaceutically acceptable salt thereof; and (b) at least one aromatase inhibitor. Such combination may be for simultaneous, separate or sequential use for the treatment of a cancer.

In the preferred embodiment, the pharmaceutical combination of the present invention comprises a compound of formula (I) selected from (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) ("Compound A") or a pharmaceutically acceptable salt thereof.

The present invention further relates to a pharmaceutical composition comprising a compound of formula (I) or a pharmaceutically acceptable salt thereof and at least one aromatase inhibitor for use in the treatment of a cancer.

The present invention further relates to the use of a pharmaceutical combination comprising a compound of formula (I) or a pharmaceutically acceptable salt thereof and at least one aromatase inhibitor, for the preparation of a medicament for the treatment of a cancer.

The present invention further relates to a method for the treatment of a cancer comprising administering to a quantity of (a) a compound of formula (I) or a pharmaceutically acceptable salt thereof, and at least one aromatase inhibitor, which is jointly therapeutically effective, to a warm-blooded animal, preferably a human, in need thereof. In accordance with the present invention, the compound of formula (I) and the aromatase inhibitor may be administered either as a single pharmaceutical composition, as separate compositions, or sequentially.

The present invention further relates to a kit comprising a compound of formula (I) according to claim 1 or a pharmaceutically acceptable salt thereof, and at least one aromatase inhibitor.

DETAILED DESCRIPTION OF THE FIGURES

DETAILED DESCRIPTION OF THE INVENTION

The present invention relates to a pharmaceutical combination comprising (a) a compound of formula (I), as defined below, or a pharmaceutically acceptable salt thereof; and (b) at least one aromatase inhibitor. Such combination may be for simultaneous, separate or sequential use for the treatment of a cancer.

The following general definitions are provided to better understand the invention:

"Combination" refers to either a fixed combination in one dosage unit form, or a non-fixed combination (or kit of parts) for the combined administration where a compound of the formula (I) and a combination partner (e.g. another active ingredient as explained below, also referred to as "therapeutic agent" or "co-agent") may be administered independently at the same time or separately within time intervals, especially where these time intervals allow that the combination partners show a cooperative, e.g. synergistic effect. The term "fixed combination" means that the active ingredients, e.g. a compound of formula (I) and a combination partner, are both administered to a patient simultaneously in the form of a single entity or dosage. The terms "non-fixed combination" or "kit of parts" mean that the active ingredients, e.g. a compound of formula (I) and a combination partner, are both administered to a patient as separate entities either simultaneously or sequentially with no specific time limits, wherein such administration provides therapeutically effective levels of the two active ingredients in the body of the patient.

"Halogen" (or "halo") denotes fluorine, bromine, chlorine or iodine, in particular fluorine, chlorine. Halogen-substituted groups and moieties, such as alkyl substituted by halogen (haloalkyl) can be mono-, poly- or per-halogenated.

"Hetero atoms" are atoms other than Carbon and Hydrogen, preferably nitrogen (N), oxygen (O) or sulfur (S), in particular nitrogen.

"Carbon containing groups", moieties or molecules contain 1 to 7, preferably 1 to 6, more preferably 1 to 4, most preferably 1 or 2, carbon atoms. Any non-cyclic carbon containing group or moiety with more than 1 carbon atom is straight-chain or branched.

The prefix "lower" or "$C_1$-$C_7$" denotes a radical having up to and including a maximum of 7, especially up to and including a maximum of 4 carbon atoms, the radicals in question being either linear or branched with single or multiple branching.

"Alkyl" refers to a straight-chain or branched-chain alkyl group, preferably represents a straight-chain or branched-chain $C_{1-12}$alkyl, particularly preferably represents a straight-chain or branched-chain $C_{1-7}$alkyl; for example, methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl, with particular preference given to methyl, ethyl, n-propyl, iso-propyl and n-butyl and iso-butyl. Alkyl may be unsubstituted or substituted. Exemplary substituents include, but are not limited to deuterium, hydroxy, alkoxy, halo and amino. An example of a substituted alkyl is trifluoromethyl. Cycloalkyl may also be a substituent to alkyl. An example of such a case is the moiety (alkyl)-cyclopropyl or alkandiyl-cycloproyl, e.g. —CH$_2$-cyclopropyl. $C_1$-$C_7$-alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or preferably methyl.

Each alkyl part of other groups like "alkoxy", "alkoxyalkyl", "alkoxycarbonyl", "alkoxy-carbonylalkyl", "alkylsulfonyl", "alkylsulfoxyl", "alkylamino", "haloalkyl" shall have the same meaning as described in the above-mentioned definition of "alkyl".

"Alkandiyl" refers to a straight-chain or branched-chain alkandiyl group bound by two different Carbon atoms to the moiety, it preferably represents a straight-chain or branched-chain $C_{1-12}$ alkandiyl, particularly preferably represents a straight-chain or branched-chain $C_{1-6}$ alkandiyl; for example, methandiyl (—CH₂—), 1,2-ethanediyl (—CH₂—CH₂—), 1,1-ethanediyl ((—CH(CH₃)—), 1,1-, 1,2-, 1,3-propanediyl and 1,1-, 1,2-, 1,3-, 1,4-butanediyl, with particular preference given to methandiyl, 1,1-ethanediyl, 1,2-ethanediyl, 1,3-propanediyl, 1,4-butanediyl.

"Alkendiyl" refers to a straight-chain or branched-chain alkendiyl group bound by two different Carbon atoms to the molecule, it preferably represents a straight-chain or branched-chain $C_{2-6}$ alkandiyl; for example, —CH=CH—, —CH=C(CH₃)—, —CH=CH—CH₂—, —C(CH₃)=CH—CH₂—, —CH=C(CH₃)—CH₂—, —CH=CH—C(CH₃)H—, —CH=CH—CH=CH—, —C(CH₃)=CH—CH=CH—, —CH=C(CH₃)—CH=CH—, with particular preference given to —CH=CH—CH₂—, —CH=CH—CH=CH—. Alkendiyl may be substituted or unsubstituted "Cycloalkyl" refers to a saturated or partially saturated, monocyclic, fused polycyclic, or Spiro polycyclic, carbocycle having from 3 to 12 ring atoms per carbocycle. Illustrative examples of cycloalkyl groups include the following moieties: cyclopropyl, cyclobutyl, cyclpentyl and cyclohexyl. Cycloalkyl may be unsubstituted or substituted; exemplary substituents are provided in the definition for alkyl and also include alkyl itself (e.g. methyl). A moiety like —(CH₃)cyclopropyl is considered substituted cycloalkyl.

"Aryl" refers to an aromatic homocyclic ring system (i.e. only Carbon as ring forming atoms) with 6 or more carbon atoms; aryl is preferably an aromatic moiety with 6 to 14 ring carbon atoms, more preferably with 6 to 10 ring carbon atoms, such as phenyl or naphthyl, preferably phenyl. Aryl may be unsubstituted or substituted by one or more, preferably up to three, more preferably up to two substituents independently selected from the group consisting of unsubstituted or substituted heterocyclyl as described below, especially pyrrolidinyl, such as pyrrolidino, oxopyrrolidinyl, such as oxopyrrolidino, $C_1$-$C_7$alkyl-pyrrolidinyl, 2,5-di-($C_1$-$C_7$alkyl)pyrrolidinyl, such as 2,5-di-($C_1$-$C_7$alkyl)-pyrrolidino, tetrahydrofuranyl, thiophenyl, $C_1$-$C_7$-alkylpyrazolidinyl, pyridinyl, $C_1$-$C_7$-alkylpiperidinyl, piperidino, piperidino substituted by amino or N-mono- or N,N-di-[lower alkyl, phenyl, $C_1$-$C_7$-alkanoyl and/or phenyl-lower alkyl)-amino, unsubstituted or N-lower alkyl substituted piperidinyl bound via a ring carbon atom, piperazino, lower alkylpiperazino, morpholino, thiomorpholino, S-oxo-thiomorpholino or S,S-dioxothiomorpholino; $C_1$-$C_7$-alkyl, amino-$C_1$-$C_7$alkyl, N—$C_1$-$C_7$alkanoylamino-$C_1$-$C_7$alkyl, N—$C_1$-$C_7$alkanesulfonyl-amino-$C_1$-$C_7$alkyl, carbamoyl-$C_1$-$C_7$alkyl, [N-mono- or N,N-di-($C_1$-$C_7$-alkyl)-carbamoyl]-$C_1$-$C_7$-alkyl, $C_1$-$C_7$alkanesulfinyl-$C_1$-$C_7$alkyl, $C_1$-$C_7$alkanesulfonyl-$C_1$-$C_7$alkyl, phenyl, naphthyl, mono- to tri-[$C_1$-$C_7$-alkyl, halo and/or cyano]-phenyl or mono- to tri-[$C_1$-$C_7$-alkyl, halo and/or cyano]-naphthyl; $C_3$-$C_8$-cycloalkyl, mono- to tri-[$C_1$-$C_7$-alkyl and/or hydroxy]-$C_3$-$C_8$-cycloalkyl; halo, hydroxy, lower alkoxy, lower-alkoxy-lower alkoxy, (lower-alkoxy)-lower alkoxy-lower alkoxy, halo-$C_1$-$C_7$-alkoxy, phenoxy, naphthyloxy, phenyl- or naphthyl-lower alkoxy; amino-$C_1$-$C_7$-alkoxy, lower-alkanoyloxy, benzoyloxy, naphthoyloxy, formyl (CHO), amino, N-mono- or N,N-di-($C_1$-$C_7$-alkyl)-amino, $C_1$-$C_7$alkanoylamino, $C_1$-$C_7$alkanesulfonylamino, carboxy, lower alkoxy carbonyl, e.g.; phenyl- or naphthyl-lower alkoxycarbonyl, such as benzyloxycarbonyl; $C_1$-$C_7$-alkanoyl, such as acetyl, benzoyl, naphthoyl, carbamoyl, N-mono- or N,N-disubstituted carbamoyl, such as N-mono- or N,N-di-substituted carbamoyl wherein the substitutents are selected from lower alkyl, (lower-alkoxy)-lower alkyl and hydroxy-lower alkyl; amidino, guanidino, ureido, mercapto, lower alkylthio, phenyl- or naphthylthio, phenyl- or naphthyl-lower alkylthio, lower alkyl-phenylthio, lower alkyl-naphthylthio, halo-lower alkylmercapto, sulfo (—SO₃H), lower alkanesulfonyl, phenyl- or naphthyl-sulfonyl, phenyl- or naphthyl-lower alkylsulfonyl, alkylphenyl-sulfonyl, halo-lower alkylsulfonyl, such as trifluoromethanesulfonyl; sulfonamido, benzosulfonamido, azido, azido-$C_1$-$C_7$-alkyl, especially azidomethyl, $C_1$-$C_7$alkanesulfonyl, sulfamoyl, N-mono- or N,N-di-($C_1$-$C_7$-alkyl)-sulfamoyl, morpholinosulfonyl, thiomorpho-linosulfonyl, cyano and nitro; where each phenyl or naphthyl (also in phenoxy or naphthoxy) mentioned above as substituent or part of a substituent of substituted alkyl (or also of substituted aryl, heterocyclyl etc. mentioned herein) is itself unsubstituted or substituted by one or more, e.g. up to three, preferably 1 or 2, substituents independently selected from halo, halo-lower alkyl, such as trifluoromethyl, hydroxy, lower alkoxy, azido, amino, N-mono- or N,N-di-(lower alkyl and/or $C_1$-$C_7$-alkanoyl)-amino, nitro, carboxy, lower-alkoxycarbonyl, carbamoyl, cyano and/or sulfamoyl.

"Heterocyclyl" refers to a heterocyclic radical that is unsaturated (=carrying the highest possible number of conjugated double bonds in the ring(s)), saturated or partially saturated and is preferably a monocyclic or in a broader aspect of the invention bicyclic, tricyclic or spirocyclic ring; and has 3 to 24, more preferably 4 to 16, most preferably 5 to 10 and most preferably 5 or 6 ring atoms; wherein one or more, preferably one to four, especially one or two ring atoms are a heteroatom (the remaining ring atoms therefore being carbon). The bonding ring (i.e. the ring connecting to the molecule) preferably has 4 to 12, especially 5 to 7 ring atoms. The term heterocyclyl also includes heteroaryl. The heterocyclic radical (heterocyclyl) may be unsubstituted or substituted by one or more, especially 1 to 3, substituents independently selected from the group consisting of the substituents defined above for substituted alkyl and/or from one or more of the following substituents: oxo (=O), thiocarbonyl (=S), imino(=NH), imino-lower alkyl. Further, heterocyclyl is especially a heterocyclyl radical selected from the group consisting of oxiranyl, azirinyl, aziridinyl, 1,2-oxathiolanyl, thienyl (=thiophenyl), furanyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidinyl, piperazinyl, pyridazinyl, morpholinyl, thiomorpholinyl, (S-oxo or S,S-dioxo)-thiomorpholinyl, indolizinyl, azepanyl, diazepanyl, especially 1,4-diazepanyl, isoindolyl, 3H-indolyl, indolyl, benzimidazolyl, cumaryl, indazolyl, triazolyl, tetrazolyl, purinyl, 4H-quinoli-zinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, benzo[1,3]di-oxol-5-yl and 2,3-dihydro-benzo[1,4]dioxin-6-yl, each of these radicals being unsubstituted or substituted by one or more, preferably up to three, substituents selected from those mentioned above for substituted aryl and/or from one or more of the following substituents: oxo (=O), thiocarbonyl (=S), imino(=NH), imino-lower alkyl.

"Arylalkyl" refers to an aryl group bound to the molecule via an alkyl group, such as a methyl or ethyl group, preferably phenethyl or benzyl, in particular benzyl. Similarly, cycloalkyl-alkyl and heterocyclyl-alkyl represents a cycloalkyl group bound to the molecule via an alkyl group or a heterocyclyl group bound to the molecule via an alkyl group. In each instance, aryl, heterocyclyl, cycloalkyl and alkyl may be substituted as defined above.

"Treatment" includes prophylactic and therapeutic treatment (including but not limited to palliative, curing, symptom-alleviating, symptom-reducing) as well as the delay of progression of a cancer disease or disorder. The term "prophylactic" means the prevention of the onset or recurrence of a cancer. The term "delay of progression" as used herein means administration of the combination to patients being in a pre-stage or in an early phase of the cancer to be treated, a pre-form of the corresponding cancer is diagnosed and/or in a patient diagnosed with a condition under which it is likely that a corresponding cancer will develop.

"Pharmaceutical preparation" or "pharmaceutical composition" refers to a mixture or solution containing at least one therapeutic agent to be administered to a warm-blooded, e.g., a human.

"Co-administer" or "combined administration" or the like are meant to encompass administration of the selected therapeutic agents (i.e., active ingredients) to a single patient, and are intended to include treatment regimens in which the agents are not necessarily administered by the same route of administration or at the same time.

"Pharmaceutically acceptable" refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

"Therapeutically effective" preferably relates to an amount of a therapeutic agent that is therapeutically or in a broader sense also prophylactically effective against the progression of a cancer.

"Jointly therapeutically effective" means that the therapeutic agents may be given separately (in a chronologically staggered manner, especially a sequence-specific manner) in such time intervals that they prefer, in the warm-blooded animal, especially human, to be treated, still show a (preferably synergistic) interaction. Whether this is the case can, inter alia, be determined by following the blood levels, showing that both therapeutic agents are present in the blood of the human to be treated at least during certain time intervals.

"Synergy", "synergistic", "synergistic interaction" or "synergistic effect" refers to the action of two therapeutic agents such as, for example, (a) a compound of formula (I) or a pharmaceutically acceptable salt thereof and (b) an aromatase inhibitor, producing an effect, for example, slowing the symptomatic progression of a cancer disease or disorder, particularly cancer, or symptoms thereof, which is greater than the simple addition of the effects of each therapeutic agent administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the therapeutic agent combination. The corresponding graphs associated with the equations referred to above are the concentration-effect curve, isobologram curve and combination index curve, respectively. Synergy may be further shown by calculating the synergy score of the combination according to methods known by one of ordinary skill.

"Single pharmaceutical composition" refers to a single carrier or vehicle formulated to deliver effective amounts of both therapeutic agents to a patient. The single vehicle is designed to deliver an effective amount of each of the therapeutic agents, along with any pharmaceutically acceptable carriers or excipients. In some embodiments, the vehicle is a tablet, capsule, pill, or a patch. In other embodiments, the vehicle is a solution or a suspension.

"Dose range" refers to an upper and a lower limit of an acceptable variation of the amount of therapeutic agent specified. Typically, a dose of the agent in any amount within the specified range can be administered to patients undergoing treatment.

"Subject", "patient", or "warm-blooded animal" is intended to include animals. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a brain tumor disease. Particularly preferred, the subject or warm-blooded animal is human.

The terms "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

Specific 2-carboxamide cycloamino urea derivatives which are suitable for the present invention, their preparation and suitable pharmaceutical formulations containing the same are described in WO 2010/029082 and include compounds of formula (I)

wherein
A represents a heteroaryl selected from the group consisting of:

$R^1$ represents one of the following substituents: (1) unsubstituted or substituted, preferably substituted $C_1$-$C_7$-alkyl, wherein said substituents are independently selected from one or more, preferably one to nine of the following moieties: deuterium, fluoro, or one to two of the following moieties $C_3$-$C_5$-cycloalkyl; (2) optionally substituted $C_3$-$C_5$-cycloalkyl wherein said substituents are independently selected from one or more, preferably one to four of the following moieties: deuterium, $C_1$-$C_4$-alkyl (preferably methyl), fluoro, cyano, aminocarbonyl; (3) optionally substituted phenyl wherein said substituents are independently selected from one or more, preferably one to two of the following moieties: deuterium, halo, cyano, $C_1$-$C_7$-alkyl, $C_1$-$C_7$alkylamino, di($C_1$-$C_7$-alkyl)amino, $C_1$-$C_7$-alkylaminocarbonyl, di($C_1$-$C_7$alkyl)aminocarbonyl, $C_1$-$C_7$-alkoxy; (4) optionally mono- or di-substituted amine; wherein said substituents are independently selected from the following moieties: deuterium, $C_1$-$C_7$-alkyl (which is unsubstituted or substituted by one or more substituents selected from the group of deuterium, fluoro, chloro, hydroxy), phenylsulfonyl (which is unsubstituted or substituted by one or more, preferably one, $C_1$-$C_7$-alkyl, $C_1$-$C_7$-alkoxy, di($C_1$-$C_7$-alkyl) amino-$C_1$-$C_7$-alkoxy); (5) substituted sulfonyl; wherein said substituent is selected from the following moieties: $C_1$-$C_7$-alkyl (which is unsubstituted or substituted by one or more substituents selected from the group of deuterium, fluoro), pyrrolidino, (which is unsubstituted or substituted by one or more substituents selected from the group of deuterium, hydroxy, oxo; particularly one oxo); (6) fluoro, chloro;

$R^2$ represents hydrogen;

$R^3$ represents (1) hydrogen, (2) fluoro, chloro, (3) optionally substituted methyl, wherein said substituents are independently selected from one or more, preferably one to three of the following moieties: deuterium, fluoro, chloro, dimethylamino, or a pharmaceutically acceptable salt thereof. The radicals and symbols as used in the definition of a compound of formula (I) have the meanings as disclosed in WO 2010/029082, which is hereby incorporated by reference in its entirety.

As disclosed in WO2010/029082, these compounds of formula (I) have been found to have significant inhibitory activity for the alpha-isoform of phosphatidylinositol 3-kinases (or PI3K). These compounds of formula (I) have advantageous pharmacological properties as a PI3K inhibitor that shows a high selectivity for the PI3-kinase alpha isoform subtype as compared to the beta and/or delta and/or gamma subtypes.

The compounds of formula (I) may be incorporated in the combination of the present invention in either the form of its free base or any salt thereof. Salts can be present alone or in mixture with free compound, e.g. the compound of the formula (I), and are preferably pharmaceutically acceptable salts. Such salts of the compounds of formula (I) are formed, for example, as acid addition salts, preferably with organic or inorganic acids, from compounds of formula (I) with a basic nitrogen atom. Suitable inorganic acids are, for example, halogen acids, such as hydrochloric acid, sulfuric acid, or phosphoric acid. Suitable organic acids are, e.g., carboxylic acids or sulfonic acids, such as fumaric acid or methansulfonic acid. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient. The salts of compounds of formula (I) are preferably pharmaceutically acceptable salts; suitable counter-ions forming pharmaceutically acceptable salts are known in the field.

In the combination of the present invention, a preferred compound of formula (I) is a compound which is specifically described in WO2010/029082. A very preferred compound of the present invention is (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) ("Compound A") or a pharmaceutically acceptable salt thereof. The synthesis of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) is described in WO2010/029082 as Example 15.

Pharmaceutical combinations of the present invention include at least one aromatase inhibitor. The expression "aromatase inhibitor" as used herein relates to a compound which inhibits the estrogen production, i.e. the conversion of the substrates androstenedione and testosterone to estrone and estradiol, respectively. Such compounds will be referred to as "aromatase inhibitors".

Suitable aromatase inhibitors include, but are not limited to,
(a) steroids, such as exemestane and formestane; and
(b) non-steroids, such as aminoglutethimide, vorozole, fadrozole, anastrozole and, especially, letrozole.

In one embodiment, the aromatase inhibitor is a steroid. In one embodiment, the aromatase inhibitor is a non-steroid.

Exemestane can be administered, e.g., in the form as it is marketed, e.g. under the trademark AROMASIN® (Pfizer Inc.). Exemestane has been specifically described in U.S. Pat. No. 4,808,616 published on Feb. 28, 1989, which is hereby incorporated by reference in its entirety. Formestane can be administered, e.g., in the form as it is marketed, e.g. under the trademark LENTARON®. Aminoglutethimide can be administered, e.g., in the form as it is marketed, e.g. under the trademark ORIMETEN® or CYTADREN®. Vorozole can be administered, e.g., in the form as it is marked, eg., under the tradename RIVIZOR® (Janssen). Fadrozole can be administered, e.g., in the form as it is marketed, e.g. under the trademark AFEMA®. Anastrozole can be administered, e.g., in the form as it is marketed, e.g. under the trademark ARIMIDEX® (AstraZeneca). Letrozole can be administered, e.g., in the form as it is marketed, e.g. under the trademark FEMARA® or FEMAR® (Novartis). Letrozole has been specifically described in the European patent No. 0 236 940 published on Sep. 16, 1987, as well as in U.S. Pat. No. 4,978,672 published on Dec. 18, 1990, and Japanese Patent No. 2018112, which are each hereby incorporated by reference in its entirety.

Preferred aromatase inhibitors for use in combination of the present invention are letrozole and/or exemestane.

The structure of the active agents identified by code nos., generic or trade names may be taken from the actual edition of the standard compendium "The Merck Index" or from databases, e.g., Patents International (e.g., IMS World Publications). The corresponding content thereof is hereby incorporated by reference.

Comprised are likewise the pharmaceutically acceptable salts thereof, the corresponding racemates, diastereoisomers, enantiomers, tautomers, as well as the corresponding crystal modifications of above disclosed compounds where present, e.g. solvates, hydrates and polymorphs, which are disclosed therein. The compounds in the combinations of the present invention can be prepared and administered as described in the cited documents, respectively. Also within the scope of this invention is the combination of more than two separate active ingredients as set forth above, i.e., a pharmaceutical combination within the scope of this invention could include three active ingredients or more.

In one embodiment of the present invention, the pharmaceutical combination comprises (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof, and at least one aromatase inhibitor selected from the group consisting of letrozole and exemestane or a pharmaceutically acceptable salt thereof.

In a further embodiment of the present invention, the pharmaceutical combination comprises (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof, and an aromatase inhibitor letrozole or a pharmaceutically acceptable salt thereof.

In a further embodiment of the present invention, the pharmaceutical combination comprises (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof, and an aromatase inhibitor exemestane or a pharmaceutically acceptable salt thereof.

It has been surprisingly discovered that the combination of a compound of formula (I), which is a highly selective alpha-isoform specific PI3K inhibitor, and at least one aromatase inhibitor possesses beneficial therapeutic properties, e.g. synergistic interaction, which render it particularly useful for the treatment of cancer. It is believed that this combination therapy will be beneficial in provoking strong anti-proliferative activity and/or strong antitumor response for the treatment of cancer.

In one aspect, the present invention relates to a pharmaceutical combination comprising (a) a compound of formula (I), preferably Compound A, or a pharmaceutically acceptable salt thereof and (b) at least one aromatase inhibitor for use in the treatment of a cancer.

Suitable cancers that can be treated with the combination of the present invention include, but are not limited to, sarcoma, lymphomas, cancer of the lung, bronchus, prostate, breast (including sporadic breast cancers and sufferers of Cowden disease), pancreas, gastrointestine, colon, rectum, colon, colorectal adenoma, thyroid, liver, intrahepatic bile duct, hepatocellular, adrenal gland, stomach, gastric, glioma, glioblastoma, endometrial, melanoma, kidney, renal pelvis, urinary bladder, uterine corpus, cervix, vagina, ovary, multiple myeloma, esophagus, a leukaemia, acute myelogenous leukemia, chronic myelogenous leukemia, lymphocytic leukemia, myeloid leukemia, brain, a carcinoma of the brain, oral cavity and pharynx, larynx, small intestine, non-Hodgkin lymphoma, melanoma, villous colon adenoma, a neoplasia, a neoplasia of epithelial character, a mammary carcinoma, basal cell carcinoma, squamous cell carcinoma, actinic keratosis, tumor diseases (including solid tumors), a tumor of the neck or head, polycythemia vera, essential thrombocythemia, myelofibrosis with myeloid metaplasia, and Waldenstroem disease. Where a cancer, a tumor, a tumor disease, sarcoma, or a cancer are mentioned, also metastasis in the original organ or tissue and/or in any other location are implied alternatively or in addition, whatever the location of the tumor and/or metastasis.

The combination of the present invention is particularly useful for the treatment of a cancer mediated by phosphatidylinositol 3-kinase (PI3K), particularly the alpha-subunit of PI3K. Proliferative diseases may include those showing overexpression or amplification of PI3K alpha, somatic mutation of PIK3CA or germline mutations or somatic mutation of PTEN or mutations and translocation of p85α that serve to up-regulate the p85-p110 complex. In a preferred embodiment, the cancer is a tumor and/or cancerous growth mediated by the alpha isoform of PI3K. Disease may include those showing overexpression or amplification of the alpha-isoform of PI3K and/or somatic mutation of PIK3CA.

The combination of the present invention is also particularly useful for the treatment of a hormone sensitive and/or hormone receptor positive cancers. Hormone sensitive cancers may include, but are not limited to, breast cancer, endometrial cancer, ovarian cancer, and/or cervical cancer. Hormone-receptor positive cancers may include estrogen receptor positive cancers (i.e., cancer that grows in response to the hormone estrogen) or progesterone receptor positive cancers (ie., cancer that grows in response to the hormone progesterone. Preferably, the hormone receptor positive cancer is estrogen receptor positive breast cancer.

In one embodiment, the cancer is a solid tumor.

In a further embodiment, the cancer is selected from the group consisting of cancer of the breast, endometrial, ovary and cervix.

In a further embodiment, the cancer is a cancer showing both (a) overexpression or amplification of the alpha-isoform of PI3K and/or somatic mutation of PIK3CA, and (b) hormone receptor positive status.

In a further embodiment, the cancer is breast cancer. Preferably, the cancer is a breast cancer having either hormone receptor positive, a mutation in the PIK3CA, or a combination thereof. More preferably, the cancer is estrogen receptor positive (+) breast cancer.

In a further embodiment, the cancer is a hormone receptor positive (+) breast cancer resistant to treatment with hormone therapy (e.g., estrogen or progesterone). A cancer "resistant to treatment with hormone therapy" refers to a cancer or tumor that either fails to respond favorably to treatment with prior hormone therapy, or alternatively, recurs or relapses after responding favorably to hormone therapy. Said hormone therapy is understood to be in the absence of a PI3K inhibitor. The cancer or tumor may be resistant or refractory at the beginning of treatment or it may become resistant or refractory during treatment.

To detect a cancer resistant to hormone therapy, a patient undergoing initial treatment can be carefully monitored for signs of resistance, non-responsiveness or recurring tumors. This can be accomplished by monitoring the patient's tumor's response to the initial treatment with the hormone therapy. The response, lack of response, or relapse of the tumor to the initial tumor can be determined by any suitable method practiced in the art. For example, this can be accomplished by the assessment of tumor size and number. An increase in tumor size or, alternatively, cancer or tumor number, indicates that the tumor is not responding to the treatment with the hormone therapy or that a relapse has occurred. The determination can be done according to the "RECIST" criteria as described in detail in Therasse et al, J. Natl. Cancer Inst. 92:205-216 (2000).

To demonstrate that the combination of the present invention is particularly suitable for the effective treatment of a cancer with good therapeutic margin and other advantages, the preclinical experiment(s) described in Examples 1 and 2 herein can be carried out by a person skilled in the art. The observation of synergy or antiproliferative activity in one species or tumor model can be predictive of the effect in other species (e.g., humans). Established correlations between tumor models and effects seen in man suggest that synergy in animals may, e.g., be demonstrated in the MCF7/Aro human breast carcinoma cell model as described in the Examples below.

Alternatively, clinical trials can be carried out in a manner known to the skilled person. Suitable clinical studies are, e.g., open label, dose escalation studies in patients with cancers. Such studies prove in particular the synergism of the active ingredients of the combination of the invention. The beneficial effects can be determined directly through the results of these studies which are known as such to a person skilled in the art. Such studies are, in particular, suitable to compare the effects of a monotherapy using the active ingredients and a combination of the invention. Preferably, the dose of active ingredient (a) is escalated until the Maximum Tolerated Dosage is reached, and active ingredient (b) is administered with a fixed dose. Alternatively, the active ingredient (a) is administered in a fixed dose and the dose of active ingredient (b) is escalated. Each patient receives doses of the active ingredient (a) either daily or intermittent. The efficacy of the treatment can be determined in such studies, e.g., after 12, 18 or 24 weeks by evaluation of symptom scores every 6 weeks.

The administration of a combination of the invention is expected to result not only in a beneficial effect, e.g., a synergistic therapeutic effect, e.g., with regard to alleviating, delaying progression of or inhibiting the symptoms, but also in further surprising beneficial effects, e.g., fewer side effects, an improved quality of life or a decreased morbidity, compared with a monotherapy applying only one of active ingredient (a) or active ingredient (b) used in the combination of the invention.

A further expected benefit is that lower doses of the active ingredients of the combination of the invention can be used, e.g., that the dosages need not only often be smaller but are also applied less frequently, which may diminish the incidence or severity of side effects. This is in accordance with the desires and requirements of the patients to be treated.

In one aspect, the present invention provides a synergistic combination for human administration comprising (a) a compound of formula (I) or a pharmaceutically acceptable salt thereof and (b) at least one aromatase inhibitor, in a combination range (w/w) which corresponds to the ranges observed in a tumor model, e.g., a tumor model described in Examples 1 or 2, used to identify a synergistic reaction. Suitably, the ratio range in humans corresponds to a non-human range selected from between 70:1 to 1:20, 70:1 to 1:12, 70:1 to 1:10, 12:1 to 1:12, 10:1 to 1:10, 7:1 to 1:6, 70:1 to 1:1, and 1:1 to 12:1.

In one aspect, the present invention relates to the use of a pharmaceutical combination comprising a compound of formula (I) or a pharmaceutically acceptable salt thereof and at least one aromatase inhibitor, for the preparation of a medicament for the treatment of a cancer.

It is understood that alternative embodiments for use of the pharmaceutical combination of the present invention those specific cancers described above for the pharmaceutical combination of the invention for use treatment of cancer, which is incorporated by reference in its entirety hereto.

In one aspect, the present invention further relates to a method for the treatment of a cancer comprising administering to a quantity of (a) a compound of formula (I) or a pharmaceutically acceptable salt thereof, and at least one aromatase inhibitor, which is jointly therapeutically effective, to a warm-blooded animal, preferably a human, in need thereof. In accordance with the present invention, the compound of formula (I) and the aromatase inhibitor may be administered either as a single pharmaceutical composition, as separate compositions, or sequentially.

It is understood that alternative embodiments for methods of treatment of the present invention include those specific cancers described above for the pharmaceutical combination of the invention for use treatment of cancer, which is incorporated by reference in its entirety hereto.

It is one objective of this invention to provide a pharmaceutical composition comprising a quantity, which is jointly therapeutically effective at targeting or preventing a cancer, of each therapeutic agent (a) and (b) of the invention. Thus, in one aspect, the present invention relates to a pharmaceutical composition comprising a compound of formula (I) or a pharmaceutically acceptable salt thereof and at least one aromatase inhibitor. In one embodiment, such pharmaceutical composition of the present invention is for use in the treatment of a cancer.

In accordance with the present invention, therapeutic agent (a) and therapeutic agent (b) may be administered together in a single pharmaceutical composition, separately in two or more separate unit dosage forms, or sequentially. The unit dosage form may also be a fixed combination.

The pharmaceutical compositions for separate administration of therapeutic agent (a) and therapeutic agent (b) or for the administration in a fixed combination (i.e., a single galenical composition comprising at least two therapeutic agents (a) and (b)) according to the invention may be prepared in a manner known per se and are those suitable for enteral, such as oral or rectal, topical, and parenteral administration to subjects, including mammals (warm-blooded animals) such as humans. Said pharmaceutical compositions comprise a therapeutically effective amount of at least one therapeutic agent alone, e.g., as indicated above, or in combination with one or more pharmaceutically acceptable carriers or diluents, especially suitable for enteral or parenteral application. Suitable pharmaceutical compositions contain, e.g., from about 0.1% to about 99.9%, preferably from about 1% to about 60%, of the active ingredient(s).

Pharmaceutical compositions for the combination therapy for enteral or parenteral administration are, e.g., those in unit dosage forms, such as sugar-coated tablets, tablets, capsules or suppositories, ampoules, injectable solutions or injectable suspensions. Topical administration is e.g. to the skin or the eye, e.g. in the form of lotions, gels, ointments or creams, or in a nasal or a suppository form. If not indicated otherwise, these are prepared in a manner known per se, e.g., by means of conventional mixing, granulating, sugar-coating, dissolving or lyophilizing processes. It will be appreciated that the unit content of therapeutic agent (a) or therapeutic agent (b) contained in an individual dose of each dosage form need not in itself constitute an effective amount since the necessary effective amount can be reached by administration of a plurality of dosage units.

Pharmaceutical compositions may comprise one or more pharmaceutical acceptable carriers or diluents and may be manufactured in conventional manner by mixing one or both combination partners with a pharmaceutically acceptable carrier or diluent. Examples of pharmaceutically acceptable diluents include, but are not limited to, lactose, dextrose, mannitol, and/or glycerol, and/or lubricants and/or polyethylene glycol. Examples of pharmaceutically acceptable binders include, but are not limited to, magnesium aluminum silicate, starches, such as corn, wheat or rice starch, gelatin, methylcellulose, sodium carboxymethylcellulose and/or polyvinylpyrrolidone, and, if desired, pharmaceutically acceptable disintegrators include, but are not limited to, starches, agar, alginic acid or a salt thereof, such as sodium alginate, and/or effervescent mixtures, or adsorbents, dyes, flavorings and sweeteners. It is also possible to use the compounds of the present invention in the form of parenterally administrable compositions or in the form of infusion solutions. The pharmaceutical compositions may be sterilized and/or may comprise excipients, for example preservatives, stabilizers, wetting compounds and/or emulsifiers, solubilisers, salts for regulating the osmotic pressure and/or buffers.

In particular, a therapeutically effective amount of each of the combination partner of the combination of the invention may be administered simultaneously or sequentially and in any order, and the components may be administered separately or as a fixed combination. For example, the method of preventing or treating a cancer according to the invention may comprise: (i) administration of the first therapeutic agent (a) in free or pharmaceutically acceptable salt form; and (ii) administration of an therapeutic agent (b) in free or pharmaceutically acceptable salt form, simultaneously or sequentially in any order, in jointly therapeutically effective amounts, preferably in synergistically effective amounts, e.g., in daily or intermittently dosages corresponding to the amounts described herein. The individual combination partners of the combination of the invention may be administered separately at different times during the course of therapy or concurrently in divided or single combination forms. Furthermore, the term "administering" also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of therapeutic agent (a) or therapeutic agent (b) employed in the combination of the invention may vary depending on the particular compound or pharmaceutical composition employed, the mode of administration, the condition being treated, the severity of the condition being treated. Thus, the dosage regimen of the combination of the invention is selected in accordance with a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the therapeutic agent required to prevent, counter or arrest the progress of the condition. Optimal precision in achieving concentration of therapeutic agent within the range that yields efficacy requires a regimen based on the kinetics of the therapeutic agent's availability to target sites. This involves a consideration of the distribution, equilibrium, and elimination of a therapeutic agent.

For purposes of the present invention, a therapeutically effective dose will generally be a total daily dose administered to a host in single or divided doses.

The compound of formula (I) may be administered to a host in a daily dosage range of, for example, from about 0.05 to about 50 mg/kg body weight of the recipient, preferably about 0.1-25 mg/kg body weight of the recipient, more preferably from about 0.5 to 10 mg/kg body weight of the recipient. For administration to a 70 kg person, the dosage range of the compound of formula (I) would be about 35-700 mg daily, and preferably, about 40-100 mg daily.

Fadrozole may be administered orally to a human in a dosage range varying from 0.5 to 10 mg/day, preferably from 1 to 2.5 mg/day.

Letrozole may be administered orally to a human in a dosage range varying from 0.5 to 5 mg/day, preferably from 0.5 to 4 mg/day, most preferably from 1 to 2.5 mg/day. Examples of compositions containing letrozole are well known in the art, e.g. Physicians' Desk Reference Copyright© 2001 (Medical Economics Company Inc).

Anastrozole may be administered orally to a human in a dosage range varying from 0.25 to 10 mg/day, preferably from 0.5 to 2.5 mg/day.

Exemestane may be administered orally to a human in a dosage range varying from 5 to 200 mg/day, preferably from 10 to 25 mg/day, or parenterally from 50 to 500 mg/day, preferably from 100 to 250 mg/day. If the therapeutic agent shall be administered in a separate pharmaceutical composition, it can be administered in the form disclosed in GB 2,177,700.

Formestane may be administered parenterally to a human in a dosage range varying from 100 to 500 mg/day, preferably from 250 to 300 mg/day.

A further benefit is that lower doses of the active ingredients of the combination of the invention can be used, e.g., that the dosages need not only often be smaller but are also applied less frequently, or can be used in order to diminish the incidence of side effects. This is in accordance with the desires and requirements of the patients to be treated.

The combination of the compound of formula (I) and at least one aromatase inhibitor can be combined in the same pharmaceutical preparation or in the form of combined preparations "kit of parts" in the sense that the combination partners can be dosed independently or by use of different fixed combinations with distinguished amounts of the combination partners, i.e., simultaneously or at different time points. The parts of the kit of parts can then, e.g., be administered simultaneously or chronologically staggered, that is at different time points and with equal or different time intervals for any part of the kit of parts.

The present invention further relates to a kit comprising a compound of formula (I), particularly (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, and at least one aromatase inhibitor, and a package insert or other labeling including directions for treating a cancer.

The present invention further relates to a kit comprising a compound of formula (I), particularly (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, and a package insert or other labeling including directions for treating a cancer by co-administering at least one aromatase inhibitor or a pharmaceutically acceptable salt thereof.

In one aspect, the present invention relates to a pharmaceutical combination comprising (a) Compound A or a pharmaceutically acceptable salt thereof, and (b) letrozole for use in the treatment of cancer, particularly breast cancer.

In one aspect, the present invention relates to a pharmaceutical combination comprising (a) Compound A or a pharmaceutically acceptable salt thereof, and (b) exemestane for use in the treatment of cancer, particularly breast cancer.

Further aspects of the invention are:
- Compounds of formula I or a pharmaceutically acceptable salt thereof in combination with at least one aromatase inhibitor for the manufacture of a medicament for use in the treatment of hormone receptor positive breast cancer, especially in patients that have acquired resistance to hormone therapy.
- A method for the treatment of hormone receptor positive breast cancer comprising administering a quantity of (a) a compound of formula (I) or a pharmaceutically acceptable salt thereof and (b) at least one aromatase inhibitor, which is jointly therapeutically effective, to a warm-blooded animal in need thereof.
- A synergistic combination for human administration comprising (a) a compound of formula (I) or a pharmaceutically acceptable salt thereof and (b) at least one aromatase inhibitor, in a w/w combination range which corresponds to a synergistic combination range of 70:1 to 1:20 parts by weight in the MCF7/Aro human breast carcinoma cells The following Examples illustrate the invention described above; they are not, however, intended to limit the scope of the invention in any way. The beneficial effects of the pharmaceutical combination of the present invention can also be determined by other test models known as such to the person skilled in the pertinent art.

EXAMPLE 1

The following experimental procedure is performed to demonstrate the efficacy and anti-proliferative activity of Compound A in combination with exemestane in the treatment of breast cancer:

Preparation of Compound Solutions:
Drugs Compound A (10 mM, in the form of its monohydrochloride salt) and exemestane (Sigma, 10 mM) are dissolved in DMSO and stored in aliquots at −20° C.

Cell Culture:
MCF7/Aro human breast carcinoma cells are stably transfected with the aromatase expression vector bearing the neomycin (G418) resistance gene. Aromatase converts the precursor androstenedione (Δ4A) into 17β-estradiol (E2), which is required for the proliferation of the host cell line. Unless otherwise mentioned, all cell culture reagents are obtained from Invitrogen. Cells are maintained in MEM (#11095-080) supplemented with 10% v/v fetal bovine serum (FBS, #10099-141), 1 mM sodium pyruvate (#11360-070), 0.5 mg/ml G418 (#10131-035) and 1% v/v non-essential amino acids (#11140-050) in a humidified incubator at 37° C. in 5% $CO_2$. The cells are passaged twice a week and the medium is changed every 2 to 3 days. To assess estrogen or androstenedione induced-cell proliferation, the medium of steroids is depleted. The steroid-depleted (SD) medium, MEM (#51200-038, without phenol red and glutamine) is supplemented with charcoal stripped FBS (#12676-029) and Glutamax (#35050-061) is used. TryPLE Express (12604-013, without phenol red) is used for cell dissociation during SD treatment.

MCF7/Aro cells are steroid deprived for 3 days before trypsinized using TryPLE Express (#12604-013, without phenol red) and 1500 cells/well are plated on clear-bottom 384-well black plates (Greiner, #781091) in triplicates with 30 μl/well growth media, cells are allowed to attach overnight and are followed by 72 hours of incubation with 10 nM of Δ4A and various concentration of therapeutic agents (or therapeutic agents (10 μl/well), and then incubation with another same dose of fresh drug or drug combinations for 48 more hours. At the end of the drug treatment, 30 μl/well of the CellTiter-Glo regent are added to each well to lyse the cells, and luminescence signals are recorded using an Envision plate reader.

Calculating the Effect of Combinations:
To evaluate the Compound A and exemestane combination effect in a non-bias way and to identify synergistic effect at all possible concentrations, the combination studies are conducted with a "dose matrix", where a combination is tested in different permutations of serially-diluted Compound A and exemestane. In all combination assays, compounds are applied simultaneously. This "dose matrix" is performed as following: Compound A is subjected to a 6 dose 3× serial dilution with the highest dose at 3 μM and the lowest dose at about 12.3 nM, and exemestane is subjected to a 7 dose 3× serial dilution with highest dose at 10 μM and lowest dose at about 13.7 nM. The synergistic interaction is analyzed using Chalice software (CombinatoRx, Cambridge Mass.). Synergy is calculated by comparing a combination's response to those of its single agents, against the drug-with-itself dose-additive reference model. Deviations from dose additives are assessed numerically with a Combination Index to quantify the overall strength of combination effects: which is essentially a volume score $V_{HSA} = \Sigma_{X,Y} \text{Inf}_X \text{Inf}_Y (I_{data} - I_{HSA})$. Also, Combination Index is also calculated between the data and the highest-single-agent surface, normalized for single agent dilution factors $f_X, f_Y$ (Lehar et al, Nature Biotechnology 27: 659-666 (2009).)

Data Analysis:
Data evaluation and graph generation is performed using Microsoft Excel software, GraphPad Prism5 software and Chalice software.

Effect of Compound A and Exemestane on Δ4A Induced MCF7/Aro Cell Proliferation:
Compound A and exemestane are evaluated as single agents and as combination for their effect on Δ4A induced MCF7/Aro cell proliferation. For single agent study, MCF7/Aro cells are seeded at 1500 cells per well in 384 well plates, and are subsequently treated with increasing concentrations of Compound A and exemestane for 5 days, CellTiter-Glo luminescence is measured and the number of relative viable cells for each treatment is calculated. The effect of each agent on Δ4A induced MCF7/Aro cell proliferation is assessed by comparing the percentage of viable cells for treated cell populations and DMSO treated control cells. Dose dependent reduction in proliferation is measured as compared to DMSO treated control cells.

To investigate the activity of a combination of Compound A and exemestane on cell proliferation in the aromatase expressing MCF7/Aro cells, a cell proliferation assay is performed with MCF7/Aro cells stimulated with 10 nM Δ4A. In order to evaluate the combination effect in a non-bias way and to identify synergistic effect at all possible concentrations, the study is conducted with a "dose matrix", where a combination is tested in different permutations of serially-diluted Compound A and exemestane. The "matrix" used in this study is as following: MCF7/Aro cells are treated in 384-well format for 5 days with Compound A and/or exemestane in the presence of Δ4A. Compound A is subjected to a 6 dose 3× serial dilution with the highest dose at 3 μM and the lowest dose at about 12.3 nM, and exemestane is subjected to a 7 dose 3× serial dilution with highest dose at 10 μM and lowest dose at about 13.7 nM. Cell viability is measured using the CellTiter-Glo assay and the percentage of inhibition is assessed over the entire dose grid. The effect of the combination on Δ4A-driven cell proliferation is demonstrated as compared to each single agent across the tested concentration range for both compounds.

Synergistic interaction is also evaluated numerically with a Combination Index quantifying the overall strength of combination effects over the entire surface. Such model compares a combination's response to those of its single agents, against the drug-with-itself dose-additive reference model, and any positive score would suggest better than dose-additive or synergy. The overall effect of synergistic interaction will be represented with Synergy Score.

Results

Following this experimental procedure, Compound A and exemestane as single agent display a concentration dependent anti-proliferative activity on Δ4A-driven cell proliferation, with the maximum level inhibition at 33% for exemestane and 61% for Compound A. When Compound A and exemestane are used in combination, the inhibition of cell proliferation is increased as compared to each agent alone across a broad range of concentrations for both compounds. The maximum level of inhibition increases to approximately 75% over a large area of dose ranges for both compound (0.12 μM-10 μM for exemestane and 0.11 μM-3 μM for Compound A).

Figure 1:
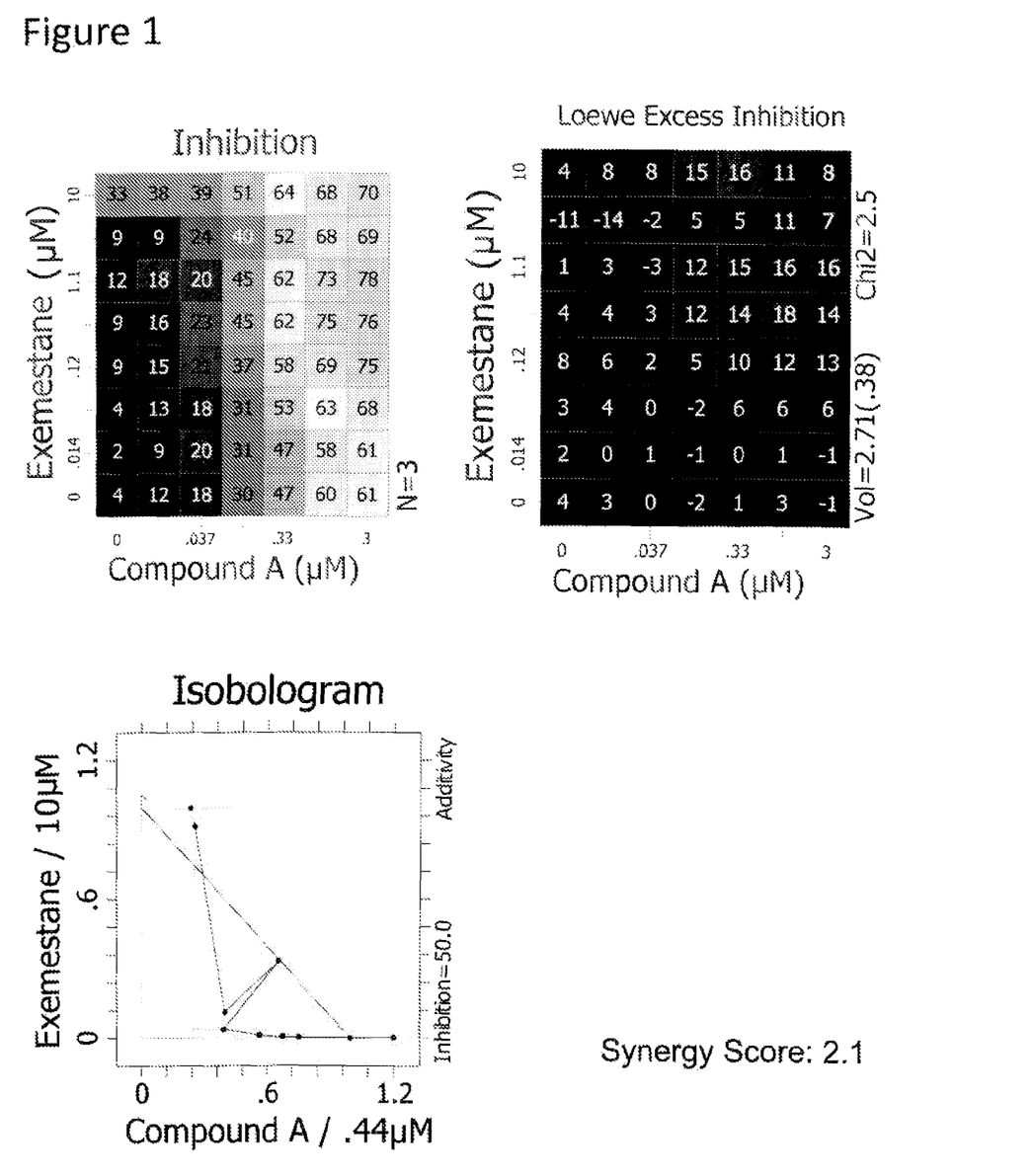
FIG. 1 shows an extended dose matrix and isobologram demonstrating the effects of combining Compound A and exemestane doses on proliferation of MCF7/ARO human breast carcinoma cells with Δ4A.

For the combination of Compound A and exemestane, synergistic interaction is also evaluated numerically with a Combination Index quantifying the overall strength of combination effects over the entire surface. Such model compares a combination's response to those of its single agents, against the drug with itself as dose-additive reference model, and any positive score is suggesting better than dose additive or synergy. The Combination Index or Synergy Score is calculated from this study as 2.1, which solidly indicates that the interaction between the Compound A and exemestane is synergistic. FIG. 1 shows the dose matrix and isobologram for this combination study of Compound A and exemestane.

EXAMPLE 2

The following experimental procedure is performed to demonstrate the efficacy and anti-proliferative activity of Compound A in combination with letrozole in the treatment of breast cancer:

Preparation of Compound Solutions:

Drugs Compound A (10 mM, in the form of its monohydrochloride salt) and letrozole (Sigma, 5 mM) are dissolved in Ethanol and stored in aliquots at −20° C.

Cell Culture:

MCF7/Aro human breast carcinoma cells are stably transfected with the aromatase expression vector bearing the neomycin (G418) resistance gene. Aromatase converts the precursor androstenedione (Δ4A) into 17β-estradiol (E2), which is required for the proliferation of the host cell line. Unless otherwise mentioned, all cell culture reagents are obtained from Invitrogen. Cells are maintained in MEM (#11095-080) supplemented with 10% v/v fetal bovine serum (FBS, #10099-141), 1 mM sodium pyruvate (#11360-070), 0.5 mg/ml G418 (#10131-035) and 1% v/v non-essential amino acids (#11140-050) in a humidified incubator at 37° C. in 5% $CO_2$. The cells are passaged twice a week and the medium is changed every 2 to 3 days. To assess estrogen or androstenedione induced-cell proliferation, the medium of steroids is depleted. The steroid-depleted (SD) medium, MEM (#51200-038, without phenol red and glutamine) is supplemented with charcoal stripped FBS (#12676-029) and Glutamax (#35050-061) is used. TryPLE Express (12604-013, without phenol red) is used for cell dissociation during SD treatment.

MCF7/Aro cells are steroid deprived for 3 days before trypsinized using TryPLE Express (#12604-013, without phenol red) and 1500 cells/well are plated on clear-bottom 384-well black plates (Greiner, #781091) in triplicates with 30 μl/well growth media, cells are allowed to attach overnight and are followed by 72 hours of incubation with 10 nM of MA and various concentration of drugs or drug combinations (10 μl/well), and then incubation with another same dose of fresh drug or drug combinations for 48 more hours. At the end of the drug treatment, 100 μl/well of the CellTiter-Glo regent are added to each well to lyse the cells, and luminescence signals are recorded using an Envision plate reader.

Calculating the Effect of Combinations:

To evaluate the Compound A and letrozole combination effect in a non-bias way and to identify synergistic effect at all possible concentrations, the combination studies are conducted with a "dose matrix", where a combination is tested in different permutations of serially-diluted Compound A and letrozole. In all combination assays, compounds are applied simultaneously. This "dose matrix" is performed as following: Compound A is subjected to a 6 dose 3× serial dilution with the highest dose at 3 μM and the lowest dose at about 12.3 nM, and letrozole is subjected to a 7 dose 3× serial dilution with highest dose at 10 μM and lowest dose at about 13.7 nM. The synergistic interaction is analyzed using Chalice software (CombinatoRx, Cambridge Mass.). Synergy is calculated by comparing a combination's response to those of its single agents, against the drug-with-itself dose-additive reference model. Deviations from dose additives are assessed numerically with a Combination Index to quantify the overall strength of combination effects: which is essentially a volume score $V_{HSA} = \Sigma_{X,Y} \text{Inf}_X \text{Inf}_Y (I_{data} - I_{HSA})$. Also, Combination Index is also calculated between the data and the highest-single-agent surface, normalized for single agent dilution factors $f_X$, $f_Y$ (Lehar et al, Nature Biotechnology 27: 659-666 (2009).)

Data Analysis:

Data evaluation and graph generation is performed using Microsoft Excel software, GraphPad Prism5 software and Chalice software.

Effect of Compound a and Letrozole on Δ4A Induced MCF7/Aro Cell Proliferation:

Compound A and letrozole are evaluated as single agents and as combination for their effect on Δ4A induced MCF7/Aro cell proliferation. For single agent study, MCF7/Aro cells are seeded at 1500 cells per well in 384 well plates, and are subsequently treated with increasing concentrations of Compound A and letrozole for 5 days, CellTiter-Glo luminescence is measured and the number of relative viable cells for each treatment is calculated. The effect of each agent on Δ4A induced MCF7/Aro cell proliferation is assessed by comparing the percentage of viable cells for treated cell populations and DMSO treated control cells. Dose dependent reduction in proliferation is measured as compared to DMSO treated control cells.

To investigate the activity of a combination of Compound A and letrozole on cell proliferation in the aromatase expressing MCF7/Aro cells, a cell proliferation assay is performed with MCF7/Aro cells stimulated with 10 nM Δ4A. In order to evaluate the combination effect in a non-bias way and to identify synergistic effect at all possible concentrations, the study is conducted with a "dose matrix", where a combination is tested in different permutations of serially-diluted Compound A and letrozole. The "matrix" used in this study is as following: MCF7/Aro cells are treated in 384-well format for 5 days with Compound A and/or letrozole in the presence of Δ4A. Compound A is subjected to a 6 dose 3× serial dilution with the highest dose at 3 μM and the lowest dose at about 12.3 nM, and letrozole is subjected to a 7 dose 3× serial dilution with highest dose at 10 μM and lowest dose at about 13.7 nM. Cell viability is measured using the CellTiter-Glo assay and the percentage of inhibition is assessed over the entire dose grid. The effect of the combination on Δ4A-driven cell proliferation is demonstrated as compared to each single agent across the tested concentration range for both compounds.

Synergistic interaction is also evaluated numerically with a Combination Index quantifying the overall strength of combination effects over the entire surface. Such model compares a combination's response to those of its single agents, against the drug-with-itself dose-additive reference model, and any positive score would suggest better than dose-additive or synergy. The overall effect of synergistic interaction will be represented with Synergy Score.

Results

Following this experimental procedure, Compound A and letrozole as single agent display a concentration dependent anti-proliferative activity on Δ4A-driven cell proliferation, with the maximum level inhibition at 53% for letrozole and 61% for Compound A. When Compound A and letrozole are used in combination, the inhibition of cell proliferation is increased as compared to each agent alone across a broad range of concentrations for both compounds. The maximum level of inhibition increases to approximately 85% over a large area of dose ranges for both compound (0.18 μM-5 μM for letrozole and 0.11 μM-3 μM for Compound A).

Figure 2:
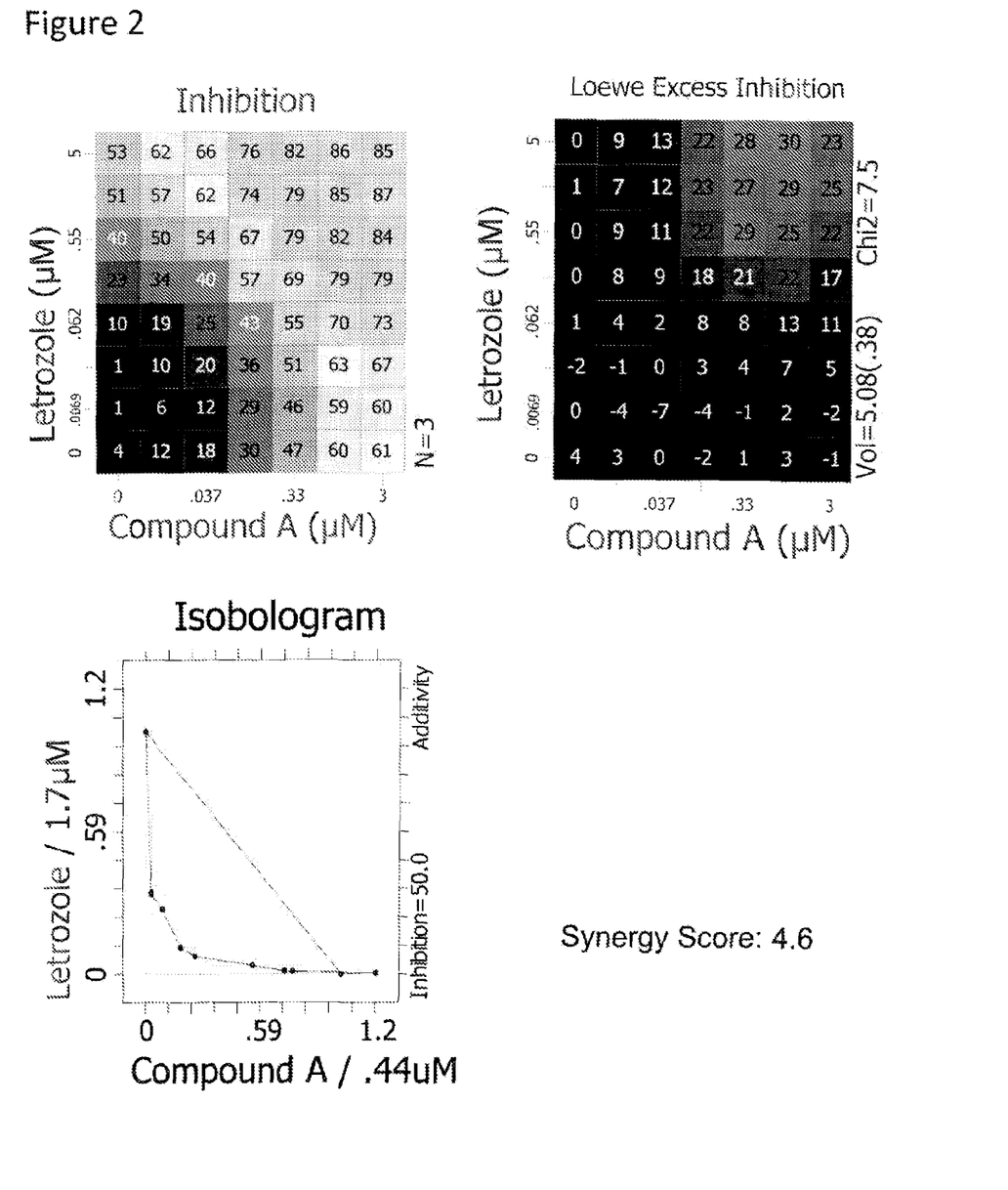
FIG. 2 shows an extended dose matrix and isobologram demonstrating the effects of combining Compound A and letrozole doses on proliferation of MCF7/ARO human breast carcinoma cells with Δ4A.

For the combination of Compound A and letrozole, synergistic interaction is also evaluated numerically with a Combination Index quantifying the overall strength of combination effects over the entire surface. Such model compares a combination's response to those of its single agents, against the drug with itself as dose-additive reference model, and any positive score is suggesting better than dose additive or synergy. The Combination Index or Synergy Score is calculated from this study as 4.6, which solidly indicates that the interaction between Compound A and letrozole is strongly synergistic. FIG. 2 shows the dose matrix and isobologram for this combination study of Compound A and letrozole.

What is claimed is:

1. A pharmaceutical combination comprising the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide)
   or a pharmaceutically acceptable salt thereof; and
   (b) at least one aromatase inhibitor which is selected from letrozole or exemestane or a pharmaceutically acceptable salt thereof for use in the treatment of breast cancer.

2. A method for the treatment of breast cancer comprising administering a quantity of (a) the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) according to claim 1 or a pharmaceutically acceptable salt thereof and (b) at least one aromatase inhibitor, which is selected from letrozole or exemestane or a pharmaceutically acceptable salt thereof, which is jointly therapeutically effective, to a warm-blooded animal in need thereof.

3. A method according to claim 2, wherein the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) and the aromatase inhibitor are administered as separate compositions or sequentially.

4. A kit comprising the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) according to claim 1 or a pharmaceutically acceptable salt thereof, and a package insert or label providing directions for treating breast cancer by co-administering at least one aromatase inhibitor.

* * * * *